United States Patent [19]

Iwata et al.

[11] Patent Number: 5,986,116
[45] Date of Patent: Nov. 16, 1999

[54] METHOD FOR PRODUCING CONJUGATED LINOLEIC ACID

[75] Inventors: Toshio Iwata; Takeshi Kamegai; Yoshie Sato; Kazumasa Watanabe; Masaaki Kasai, all of Nagoya, Japan

[73] Assignee: Rinoru Oil Mills Co., Ltd., Tokyo-to, Japan

[21] Appl. No.: 08/957,774

[22] Filed: Oct. 24, 1997

[30] Foreign Application Priority Data

Oct. 30, 1996 [JP] Japan ................................. 8-288094

[51] Int. Cl.$^6$ ................................................ C07B 35/08
[52] U.S. Cl. ............................................................ 554/126
[58] Field of Search ............................................ 554/126

[56] References Cited

U.S. PATENT DOCUMENTS 3,984,444  10/1976  Ritz et al. .................. 554/126
4,164,505  8/1979  Krajca ......................... 554/126
5,208,358  5/1993  Pariza et al. .

FOREIGN PATENT DOCUMENTS 0 778 033    6/1997   European Pat. Off. .
54 095 502 A 7/1979   Japan .

OTHER PUBLICATIONS

G.S.R. Sastry et al. "Isomerised Safflower Oil", *Paint Manufacture*, vol. 40, No. 8, 1970, pp. 32–34.

C.R. Scholfield et al., "Cyclization of linolenic Acid by Alkali Isomerization", *Journal of The American Chemists'Society*, vol. 36, No. 12, 1959, pp.631–635.

*Primary Examiner*—James O. Wilson
*Assistant Examiner*—Deborah D Carr
*Attorney, Agent, or Firm*—Foley & Lardner

[57] ABSTRACT

There is provided a method for producing conjugated linoleic acid, comprising subjecting a fat or oil containing linoleic acid to alkali isomerization reaction in an alkali-propylene glycol solution.

4 Claims, 1 Drawing Sheet

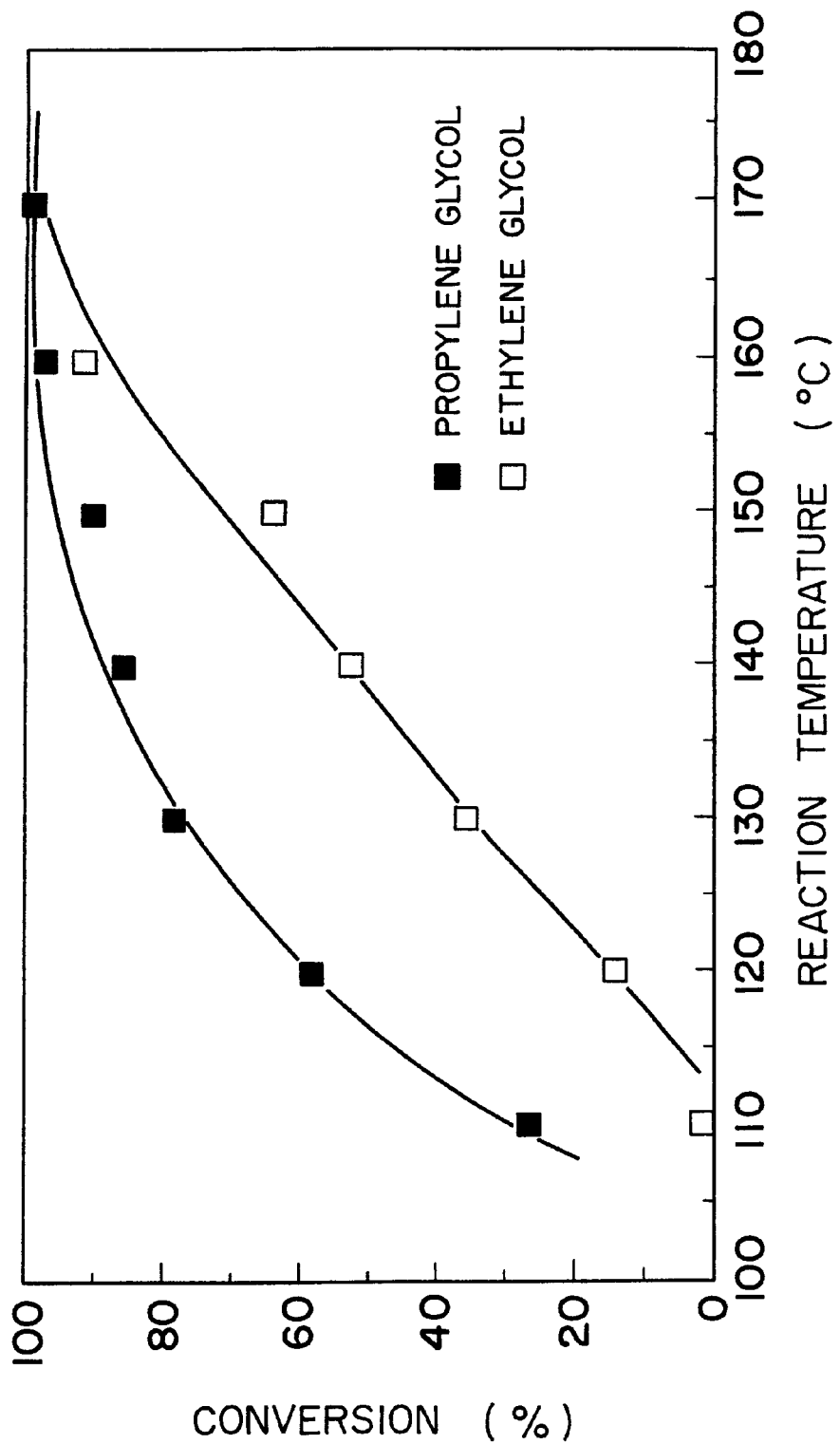
F I G. I

METHOD FOR PRODUCING CONJUGATED LINOLEIC ACID

BACKGROUND OF THE INVENTION

1. Field of the Invention

This invention relates to a method for producing conjugated linoleic acid. More particularly, this invention relates to a method for efficiently transforming the linoleic acid contained in a fat or oil into conjugated linoleic acid by carrying out the alkali isomerization of the linoleic acid in a specific solvent.

2. Background Art

As a method for producing conjugated fatty acids, the so-called "alkali isomerization" method is known, in which an organic solvent, typically ethylene glycol, is employed (J. Am. Oil Chem. Soc., 36, 631 (1959); The 34th Annual Meeting on Oil Chemists' Society, p. 171 (1995); and "Standard Methods for the Analysis of Fats, Oils and Related Materials", 2.4.16–17). It is reported in the J. Am. Oil Chem. Soc., 36, 631 (1959) that, when methyl linolenate was heated in a potassium hydroxide-ethylene glycol solution at 200° C. for 7 hours, about 80% conversion (conjugation) was attained. However, the reported method also involves cyclization and other side reactions.

According to the 34th Annual Meeting on Oil Chemist's Society, p. 171 (1995), tests were carried out in accordance with the method described in the "Standard Methods for the Analysis of Fats, Oils and Related Materials", 2.4.16–17, and the following are reported: when methyl linolate was allowed to react in a potassium hydroxide-ethylene glycol solution at 180° C. for 2 hours, the rate of the conjugated diene formed reached approximately 80% or more, and the amount of potassium hydroxide used in this reaction was six times the number of moles of 1,4-butadiene structure; and, when a safflower oil was subjected to isomerization reaction at 30° C. for 1.5 hours by using, as solvents, dimethyl sulfoxide and dimethylformamide, and, as an alkali, sodium methoxide (in an amount of two times the number of moles of 1,4-butadiene structure), the rate of the conjugated diene formed reached approximately 73%.

Among the three types of solvents reported in the above reference, ethylene glycol is most preferred from the viewpoint of alkali solubility (in the case of the other two solvents, the type of alkalis which can be used is limited, and, the solvents must be used in a large amount).

As discussed above, in the conventional alkali isomerization methods for producing conjugated fatty acids, ethylene glycol, dimethyl sulfoxide or dimethylformamide is used as a solvent. However, these three compounds all have some toxicity. The conventional methods thus have the drawback that the resulting conjugated products cannot be used for foods.

It is therefore an object of the present invention to provide a method for producing conjugated linoleic acid, which can more efficiently transform linoleic acid into conjugated linoleic acid and which makes it possible to use the conjugated product in the field of foods.

SUMMARY OF THE INVENTION

It has now been found by the present inventors that the above object can be attained by using propylene glycol as a solvent in the production of conjugated linoleic acid by the alkali isomerization method.

Thus, the method for producing conjugated linoleic acid according to the present invention comprises subjecting a fat or oil containing linoleic acid to alkali isomerization reaction in an alkali-propylene glycol solution.

The method of the present invention, which utilizes propylene glycol as a solvent, can produce conjugated linoleic acid in a higher yield as compared with the conventional method which uses ethylene glycol, the most preferred solvent conventionally known. In addition, the method of the present invention has the further advantage that the resulting fat or oil containing the conjugated linoleic acid is less colored. Moreover, since propylene glycol is not toxic, the product according to the present invention can be used for foods.

BRIEF DESCRIPTION OF THE DRAWING

FIG. 1 is a graph showing the rate of conversion of linoleic acid into conjugated linoleic acid with respect to the products obtained in Examples and Comparative Examples.

DETAILED DESCRIPTION OF THE INVENTION

According to the method of the present invention, a fat or oil containing linoleic acid is subjected to alkali isomerization reaction carried out in an alkali-propylene glycol solution, whereby the linoleic acid contained in the fat or oil is converted or transformed into conjugated linoleic acid. As the fat or oil containing linoleic acid, any fat or oil such as safflower oil, sunflower oil, corn oil, soybean oil, cottonseed oil, linseed oil or wheat germ oil can be used as long as it contains linoleic acid. Of these, safflower oil and sunflower oil, both having high linoleic acid contents, are preferred.

Examples of the alkali usable in the present invention include potassium hydroxide, sodium methoxide, sodium hydroxide and t-butyl alkoxide. Of these, potassium hydroxide and sodium methoxide are preferred. The alkali may be used generally in an amount of from 1 to 8 times, preferably from 3 to 6 times the number of moles of the linoleic acid contained in the fat or oil.

In the method of the present invention, the amount of propylene glycol, which is used as a solvent, is generally from 1 to 10 times, preferably from 1.5 to 5 times the weight of the fat or oil containing linoleic acid.

The isomerization reaction for transforming the linoleic acid contained in the fat or oil into conjugated linoleic acid is carried out in a solution of the above-described alkali in propylene glycol under a stream of nitrogen. The reaction temperature is generally from 110 to 180° C., preferably from 130 to 170° C. The reaction time is generally from 1 to 5 hours, preferably from 2 to 3 hours. As shown in Examples which will be described later, conjugated linoleic acid can be produced at a high conversion of 80% or more, when the reaction is carried out under the above-described preferable reaction temperature condition.

According to the method of the present invention using, as a solvent, propylene glycol which is not harmful for the human body, the resulting product can be applied not only to conventional uses such as additives for rubbers and insulating materials for IC, but also to foods such as muscle-enhancing agents and nutrition-replenishing foods, for which the products obtained by the conventional alkali isomerization methods cannot be used.

EXAMPLES

The following examples illustrate the present invention but are not intended to limit it.

Example 1

50 g of potassium hydroxide was dissolved in 150 g of propylene glycol. Nitrogen gas was blown into the solution for 20 minutes, and the temperature of the solution was raised to 110° C. Thereafter, 100 g of a safflower oil was added to the solution, and allowed to react at 110° C. for 2.5 hours under a stream of nitrogen (the fatty acid composition of the safflower oil used is shown in Table 1). After the reaction was completed, the reaction mixture was cooled to room temperature, and made neutral by the addition of hydrochloric acid. The mixture was stirred for 15 minutes. Subsequently, the pH of the reaction mixture was adjusted to 3, to which distilled water was added. The resulting mixture was stirred for 5 minutes, and then subjected to extraction with hexane three times. The hexane solution was washed with a 5% NaCl solution and with distilled water, followed by dewatering and filtration. Thereafter, the hexane was distilled off to obtain a product containing conjugated linoleic acid. The conjugated linoleic acid content of the product obtained was measured by gas chromatography, thereby determining the rate of conversion of linoleic acid into conjugated linoleic acid. The conversion determined was 26.5%. Further, the degree of the coloring of the product was measured by the Gardner method (ASTM D1544). As a result, the product was found to have a Gardner color standard number of 3.

TABLE 1

Fatty Acid Composition of Safflower Oil (%)

| Fatty Acid | Before Reaction | After Reaction |
| --- | --- | --- |
| Palmitic acid | 7.0 | 7.0 |
| Stearic acid | 2.6 | 2.6 |
| Oleic acid | 14.4 | 14.4 |
| Linoleic acid | 76.0 | 55.9 |
| Conjugated linoleic acid | 0 | 20.1 |

Examples 2 to 7

The procedure of Example 1 was repeated except that the reaction temperature was changed to 120° C. (Example 2), 130° C. (Example 3), 140° C. (Example 4), 150° C. (Example 5), 160° C. (Example 6) and 170°0 C. (Example 7), thereby obtaining products containing conjugated linoleic acid. For the products thus obtained, the rate of conversion of linoleic acid into conjugated linoleic acid and the Gardner color standard number were measured. The results are shown in Tables 2 and 3.

Comparative Examples 1 to 7

The procedures of Examples 1 to 7 were respectively repeated except that the solvent was changed from propylene glycol to ethylene glycol, thereby obtaining products containing conjugated linoleic acid. The results of the above measurements are shown in Tables 2 and 3.

TABLE 2

Rate of Conversion (%)

| Reaction Temp. (° C.) | Propylene Glycol | Ethylene Glycol |
| --- | --- | --- |
| 110 | 26.5 (Ex. 1) | 1.6 (Comp. Ex. 1) |
| 120 | 58.4 (Ex. 2) | 14.1 (Comp. Ex. 2) |
| 130 | 78.2 (Ex. 3) | 35.7 (Comp. Ex. 3) |
| 140 | 85.7 (Ex. 4) | 52.8 (Comp. Ex. 4) |
| 150 | 90.0 (Ex. 5) | 63.9 (Comp. Ex. 5) |
| 160 | 97.2 (Ex. 6) | 91.5 (Comp. Ex. 6) |
| 170 | 99.1 (Ex. 7) | 99.0 (Comp. Ex. 7) |

TABLE 3

Gardner Color Standard Number

| Reaction Temp. (° C.) | Propylene Glycol | Ethylene Glycol |
| --- | --- | --- |
| 110 | 3 (Ex. 1) | 9 (Comp. Ex. 1) |
| 120 | 3 (Ex. 2) | 9 (Comp. Ex. 2) |
| 130 | 3 (Ex. 3) | 9 (Comp. Ex. 3) |
| 140 | 3 (Ex. 4) | 8 (Comp. Ex. 4) |
| 150 | 3 (Ex. 5) | 8 (Comp. Ex. 5) |
| 160 | 2 (Ex. 6) | 6 (Comp. Ex. 6) |
| 170 | 2 (Ex. 7) | 5 (Comp. Ex. 7) |

The relationship between the reaction temperatures and the rates of conversion of linoleic acid into conjugated linoleic acid tabulated in Table 2 is graphically shown in FIG. 1. As is apparent from FIG. 1, the method of the present invention, which uses propylene glycol as a solvent, attains considerably higher rates of conversion of linoleic acid into conjugated linoleic acid, as compared with the conventional method using ethylene glycol as a solvent. The difference in the rate of conversion between the two methods is marked when the reaction temperature is 150° C. or lower. Further, as may be appreciated from Table 3, the products containing conjugated linoleic acid obtained by the method of the present invention are much less colored, compared to the products obtained by the conventional process (Gardner color standard number 2: light yellow—Gardner color standard number 9: brown).

What is claimed is:

1. A method for producing conjugated linoleic acid, comprising subjecting a fat or oil containing linoleic acid to alkali isomerization reaction in an alkali-propylene glycol solution.

2. The method according to claim 1, wherein the fat or oil containing linoleic acid is selected from the group consisting of safflower oil, sunflower oil, corn oil, soybean oil, cottonseed oil, linseed oil and wheat germ oil.

3. The method according to claim 1, wherein the alkali is potassium hydroxide or sodium methoxide.

4. The method according to claim 1, wherein the reaction is carried out at a temperature of 130 to 170° C.

* * * * *